(12) United States Patent
Frank

(10) Patent No.: US 8,007,531 B2
(45) Date of Patent: *Aug. 30, 2011

(54) IMPLANTABLE PROSTHESIS FOR POSITIONING AND SUPPORTING A BREAST IMPLANT

(76) Inventor: Robert E. Frank, Chicago, IL (US)

( * ) Notice: Subject to any disclaimer, the term of this patent is extended or adjusted under 35 U.S.C. 154(b) by 1136 days.

This patent is subject to a terminal disclaimer.

(21) Appl. No.: 11/564,627

(22) Filed: Nov. 29, 2006

(65) Prior Publication Data

US 2007/0088434 A1   Apr. 19, 2007

Related U.S. Application Data

(63) Continuation-in-part of application No. 11/196,217, filed on Aug. 3, 2005, now Pat. No. 7,476,249.

(60) Provisional application No. 60/599,512, filed on Aug. 6, 2004.

(51) Int. Cl.
*A61F 2/12* (2006.01)
(52) U.S. Cl. .......................................................... 623/8
(58) Field of Classification Search .................. 623/7, 8
See application file for complete search history.

(56) References Cited

U.S. PATENT DOCUMENTS

| 4,648,880 | A | | 3/1987 | Brauman |
|---|---|---|---|---|
| 4,820,303 | A | | 4/1989 | Brauman |
| 4,840,629 | A | * | 6/1989 | Bustos ............................. 623/8 |
| 4,936,858 | A | | 6/1990 | O'Keeffe |
| 4,955,907 | A | | 9/1990 | Ledergerber |
| 5,147,374 | A | | 9/1992 | Fernandez |
| 5,282,856 | A | | 2/1994 | Ledergerber |
| 5,356,429 | A | | 10/1994 | Seare |
| 5,569,273 | A | | 10/1996 | Titone et al. |
| 5,954,767 | A | | 9/1999 | Pajotin |
| 6,113,634 | A | | 9/2000 | Weber-Unger et al. |
| 6,258,124 | B1 | | 7/2001 | Darcis et al. |
| 6,306,079 | B1 | | 10/2001 | Trabucco |

(Continued)

FOREIGN PATENT DOCUMENTS

FR   2682284 A1   10/1991

(Continued)

OTHER PUBLICATIONS

Coapt Systems, Inc., brochure, "Endotine For All Brow and Forehead Lift Procedures", 2005, 7 pages.

(Continued)

*Primary Examiner* — Thomas J Sweet
*Assistant Examiner* — Seema Swaminathan
(74) *Attorney, Agent, or Firm* — Leydig, Voit & Mayer, Ltd.

(57) ABSTRACT

An implantable prosthesis for use in positioning a breast implant comprising a sheet of a prosthetic material configured to form a sling-shaped receiving area for receiving and supporting the breast implant. The surface area of the implantable prosthesis contacting the breast implant comprises a biocompatible or chemically inert material to prevent abrasion of or reaction with the breast implant. The implantable prosthesis of the present invention can be used during corrective procedures to reposition and support a malpositioned breast implant or during reconstructive or cosmetic procedures at the time the implant is first positioned within the patient. The prosthesis is used with implants in the partial sub-muscular, completely sub-muscular, and sub-glandular position and is used to prevent medial, lateral and inferior displacement of the implant.

13 Claims, 11 Drawing Sheets

U.S. PATENT DOCUMENTS

| | | |
|---|---|---|
| 6,350,285 B2 | 2/2002 | Gerlach et al. |
| 6,383,301 B1 | 5/2002 | Dong |
| 6,648,921 B2 | 11/2003 | Anderson et al. |
| 6,692,527 B1 | 2/2004 | Bellin et al. |
| 2002/0072694 A1 | 6/2002 | Snitkin et al. |
| 2003/0212462 A1 | 11/2003 | Gryska et al. |
| 2004/0015041 A1 | 1/2004 | Melvin |
| 2004/0054253 A1 | 3/2004 | Snitkin et al. |
| 2004/0127985 A1 | 7/2004 | Bellin et al. |

FOREIGN PATENT DOCUMENTS

| | | |
|---|---|---|
| WO | WO90/00888 | 2/1990 |
| WO | WO 98/00888 A1 | 2/1990 |
| WO | WO2004/096098 | 11/2004 |
| WO | WO 2006/017834 A2 | 2/2006 |

OTHER PUBLICATIONS

Coapt Systems, Inc., brochure, "Endotine Midface", 2005, 6 pages.
Coapt Systems, Inc., website pages, Endotine product description, www.coaptsystems.com, 9 pages, printed Nov. 29, 2006.
Lifecell Corporation, website pages, AlloDerm product, www.lifecell.com, 10 pages, printed Nov. 7, 2006.
Shana Ting Lipton, Boobs of Steel, Wired Magazine, Oct. 2004, p. 334 vol.-Issue 12.10, Conde Nast Publications, New York, USA.
Calvert Collins, Doctor uses metal in breat implants, CNN.com Health, Jul. 19, 2004, (www.cnn.com/2004/Health/07/19/breast.implants).
Thea Jordan, What a Lovely Pair of Titaniums originally published Jun. 24, 2004, http://www.int.iol.co.za/index.php?set_id=1&click_id=117&art_id=vn20040624134145788C105826.
International Search Report, PCT/US05/28187, Jul. 13, 2006.
Written Opinion of International Searching Authority, PCT/US05/28187, Jul. 13, 2006.
International Search Report, PCT/US2007/024563, Mar. 31, 2008.
Written Opinion of International Searching Authority, PCT/US2007/024563, Mar. 31, 2008.
Baxter, "Intracapsular Allogenic Dermal Grafts for Breast Implant-Related Problems," *Plastic and Reconstructive Surgery*, Nov. 2003, pp. 1692-1696, vol.-Issue 112.6.
Duncan, "Correction of Implant Rippling Using Allograft Dermis," *Aesthetic Surgery Journal*, Jan./Feb. 2001, pp. 81-84, vol.-Issue 21.1.
Góes, "Periareolar Mammaplasty: Double Skin Technique with Application of Polyglactine or Mixed Mesh," *Plastic and Reconstructive Surgery*, Apr. 1996, pp. 959-968, vol.-Issue 97.5.
Góes, "Periareolar Mastopexy and Reduction with Mesh Support," *Surgery of the Breast: Principles and Art*, Spear (ed.), 1998, pp. 697-708, Lippincott-Raven, Philadelphia.

\* cited by examiner

IMPLANTABLE PROSTHESIS FOR POSITIONING AND SUPPORTING A BREAST IMPLANT

CROSS-REFERENCE TO RELATED APPLICATIONS

This application is a continuation-in-part of U.S. patent application Ser. No. 11/196,217, filed on Aug. 3, 2005, which claims priority to U.S. Provisional Patent Application Ser. No. 60/599,512, filed on Aug. 6, 2004.

BACKGROUND OF INVENTION

1. Field of Invention

The present invention relates to an implantable prosthesis for positioning and supporting a breast implant within a patient and a method of positioning and supporting the breast implant within the patient using the implantable prosthesis.

2. Description of Related Art

The American Society of Plastic Surgeons reports that breast augmentation procedures increased seven-fold in the ten-year period between 1992 and 2002, increasing from 32,607 procedures in 1992 to 225,818 procedures in 2002. Overall it has been estimated from breast implant sales data that anywhere between 1.5 to more than 2 million women in the United States alone have breast implants. An estimated 70-80% of breast augmentation procedures were performed for cosmetic purposes while the remaining 20-30% were performed for reconstructive purposes.

Implants are positioned within the chest in one of three positions: (1) implant over the pectoralis major muscle and under the breast tissue (subglandular); (2) implant partially under the muscle (partial submuscular); and (3) implant completely under the muscle (submuscular). The subglandular placement puts the implant directly behind the breast tissue and mammary gland and in front of the pectoralis major muscle. This placement requires the least complicated surgery and yields the quickest recovery. The downsides of this placement are increased chances for capsular contracture, greater visibility and vulnerability for the implant. This is because only the skin and breast tissue separate the implant from the outside world. Depending on the amount of available breast tissue the implant may be seen "rippling" through the skin.

Partial submuscular placement involves placing the implant under the pectoralis major muscle. Because of the structure of this muscle, the implant is only partially covered. This alternative reduces the risk of capsular contracture and visible implant rippling, but recovery time from this positioning is typically longer and more painful because the surgeon has to manipulate the muscle during surgery. Also, because of increased swelling, the implant may take longer to drop into a natural position after surgery. Completely submuscular placements puts the implant firmly behind the chest muscle wall. The implant is placed behind the pectoralis major muscle and behind all of the supporting fascia (connective tissue) and non-pectoral muscle groups. This placement has even longer recovery time, potential loss of inferior pole fullness, and involves a more traumatic surgical procedure.

Regardless of location of the implant, in the case of breast augmentation the surgery is carried out through an incision placed to minimize long-term scarring. The incision is made in one of three areas: (1) peri-areolar incision; (2) inframammary fold incision; and (3) transaxillary incision. The peri-areolar incision enables the surgeon to place the implant in the subglandular partial submuscular or completely submuscular position, with the implant being inserted, or removed, through the incision. Like the peri-areolar incision, the inframammary fold incision provides for all three placement types and both insertion and removal of the implant through the incision. The incision is made in the crease under the breast, allowing for discreet scarring. Once the incision is made, the implant is inserted and worked vertically into place.

The transaxillary incision is made in the armpit. The incision is made in the fold of the armpit and a channel is cut to the breast. The implant is inserted into the channel and worked into place. Like the peri-areolar and crease incisions, the armpit incision can be used for implant placement anywhere in the breast. If a complication occurs that requires revision or removal of the implant, the surgeon will likely have to make a peri-areolar or inframammary fold incision to revise the position of the implant. The transaxillary incision is rarely reused because it is difficult to work on an implant from what is really a remote site. Visibility inside the breast is extremely limited for the surgeon with a transaxillary incision without the use of a fiber optic endoscope, which can be cumbersome in a revisional setting. In the case of reconstructive procedures, the patient's prior mastectomy incision is often used.

Once the incision is created, the surgeon must cut a path through the tissue to the final destination of the implant. Once that path has been created, the tissue and/or muscle (depending on placement) must be separated to create a pocket for the implant. When deciding where to cut the pocket in the breast, the surgeon must predict what the breasts will look like when the implants are filled.

Presently, there are very few techniques to reliably maintain the position of implants placed as part of cosmetic or reconstructive surgical procedures. Implant malposition may be the result of several factors, including poor surgical technique, i.e. the implant pocket is too big or too low; implant weight; or lack of soft tissue support. In addition, in reconstructive patients cancer treatments, such as chemotherapy, weaken the soft tissue and surgery, in general, interrupts the natural anatomic plains of the soft tissue. These factors are more profound in patients who have lost massive amounts of weight. Such situations typically provide extremely poor soft tissue support and the inability of the usual support structures within the breast, such as the inframammary fold, to support the weight of the implant.

Patient studies have demonstrated an 8-12% incidence of implant malposition severe enough to incur removal of the implant within 5 years. Over time, implants can be displaced medially resulting in symmastia (as is seen in FIG. 1), laterally resulting in implant excursion into the axilla of the chest cavity, or inferiorly resulting in "bottoming out" (as is seen in FIG. 2).

Symmastia is commonly referred to as "bread loafing" and is commonly seen in patients who have subglandular implants. With this condition, the implant pockets actually meet in the middle of the chest, giving the appearance of one breast 2 (FIG. 1), instead of two. The condition is most often related to technical error by a surgeon attempting to create too much cleavage in the patient or using an overly wide implant. Lateral displacement results in the implant moving into the armpit, especially when the patient is lying flat on her back. Lateral displacement is most common with submuscular placement when muscle is inadequately released medially and is the most under-recognized implant displacement problem.

Inferior displacement or "bottoming out" is described as a lengthening of the distance from the nipple to inframammary fold. This type of displacement results from a lowering of the inframammary fold during surgery or an inadequacy of soft tissue support required to maintain the implant weight. FIG. 2 shows a breast implant 4 that has bottomed out after submuscular placement within the patient. FIG. 2 also shows the proper location of an implant 6 that has not bottomed out. Bottoming out of implants may be exacerbated by a failure to wear a bra, activities resulting in excessive "bouncing" of the implants, excessively large implants, and/or extreme weight loss. Once these problems are established, classical repair techniques have had limited effectiveness, with high rates of displacement recurrence.

The traditional method of correction for implant malposition has utilized the scar tissue "capsule" as the strength of the repair. In most descriptions, the capsule is allowed several months to "mature" at which point the patient is taken to surgery, a section of the scar capsule excised or imbricated on itself and the remaining capsule closed using non-resorbable sutures.

The problems with this method are numerous. First, the scar capsule is often attenuated making adequate "bites" of capsule impossible. Second, the capsule is itself distensible so the factors which initially acted on the pocket can result in rapid recurrence. Finally, and most obviously, in nearly all cases the implant is replaced once the repair is complete—once again putting strain on the repair especially in the case of bottoming out. Some authors have advocated the use of percutaneous bolsters 8 (seen in FIGS. 3 and 4) placed to buttress the repair and take pressure off the internal repair. These bolsters may limit direct implant pressure but leave unattractive scars on the skin due to the tension. For medial malposition, the use of a Thongbra® (a bra designed to apply pressure over the sternum) or bolsters placed to secure the medial breast skin to the underlying sternum have had limited success.

BRIEF SUMMARY OF INVENTION

The present invention comprises an implantable prosthesis for positioning a breast implant within a patient, where the prosthesis comprises a sheet of prosthetic material configured to form a receiving area for receiving the breast implant, and comprising at least a first tissue affixation region. The first tissue affixation region is adapted to attach the implantable prosthesis to soft tissue surrounding the breast implant or a boney structure within the patient, such as the periosteum of the chest cavity, with a first suture or by conventional or endoscopic tacking. Preferably, the sheet of prosthetic material is of a porous nature to facilitate tissue in growth and secure fixation of the implantable prosthesis to the patient. The outer surface of the prosthetic material is composed of polytetrafluoroethylene, silicone, or another suitable chemically inert material.

In one preferred embodiment of the present invention, a biocompatible landing overlays the prosthetic material, the landing adopted to communicate with and support the breast implant. The landing is composed of a pad overlaying the receiving area, the pad being composed of polytetraflouroethylene, silicone, or any other suitable chemically inert material. The landing pad is affixed to the sheet by stitching, a biocompatible, inert adhesive, or any other suitable means of attachment. In another preferred embodiment, the receiving area comprises the fibers of the porous sheet of prosthetic material and the landing comprises coating the fibers with polytetraflouroethylene, silicone, or any other suitable chemically inert material.

The present invention also comprises a method of maintaining the position of a breast implant with an implantable prosthesis, the method comprising: providing a sheet of prosthetic material comprising a front surface configured to form a receiving area for receiving the breast implant, and providing at least a first tissue affixation region adapted to facilitate fixation of the implantable prosthesis to the patient. The sheet of prosthetic material is provided with an outer surface composed of a biocompatible material comprising polytetrafluoroethylene, silicone, or another suitable, chemically inert material.

The method further comprises cutting an incision in a patient, the incision adapted to provide a point of insertion for the breast implant, the method further comprising rolling the implantable prosthesis up and inserting the prosthetic through the incision, wherein the incision is a peri-areolar incision or an infra-mammary incision. The first end of the sheet of prosthetic material is sutured to an area of soft tissue surrounding the breast implant. The implantable prosthesis is then unfurled, positioned, and affixed to the patient at the first tissue affixation region with a suture or by conventional or endoscopic tacking. The sheet of prosthetic material is preferably a porous mesh to facilitate tissue in growth to securely hold the implantable prosthesis in place.

DETAILED DESCRIPTION OF INVENTION

The current innovation calls for the development of an implantable prosthesis in the form of a support sling for use in cosmetic and reconstructive breast surgery. This implantable prosthesis would not be used to hold native breast tissue in place but rather to minimize the amount of implant displacement. Most implants placed for reconstruction and augmentation are placed in the sub-muscular position. From this position, an implantable prosthesis placed medially, laterally, or inferiorly would be in contact solely with the muscles of the chest wall and would not be directly in contact with breast parenchyma.

The implantable prosthesis of the present invention can be utilized during corrective procedures to reposition a malpositioned implant or as a prophylactic measure during procedures wherein the implant is initially placed and positioned within the patient. As is shown, in FIGS. 5 and 6, the implantable prosthesis 10 comprises a sheet 12 of prosthetic material, which is preferably porous and will benefit from incorporation into the surrounding tissues over time, taking the point of tension off individual sutures placed in weakened soft tissue and transfer the tension more broadly across the anterior and posterior surfaces of the implantable prosthesis' points of contact with the body. The contour of the involved surface would also be cosmetically improved since the implantable prosthesis could be fixed at the extremes of the repair and allowed to "drape" along the involved segment, limiting the unnatural depressions associated with suture bites along the repaired segment. The optimal material for the implantable prosthesis possesses the following characteristics: (1) porous portions enabling tissue integration and in growth over time; (2) inert with respect to the implant material; (3) soft; (4) minimal palpability; (5) easily cut to size; (6) holds shape; and (7) cost effective.

Figure 1:
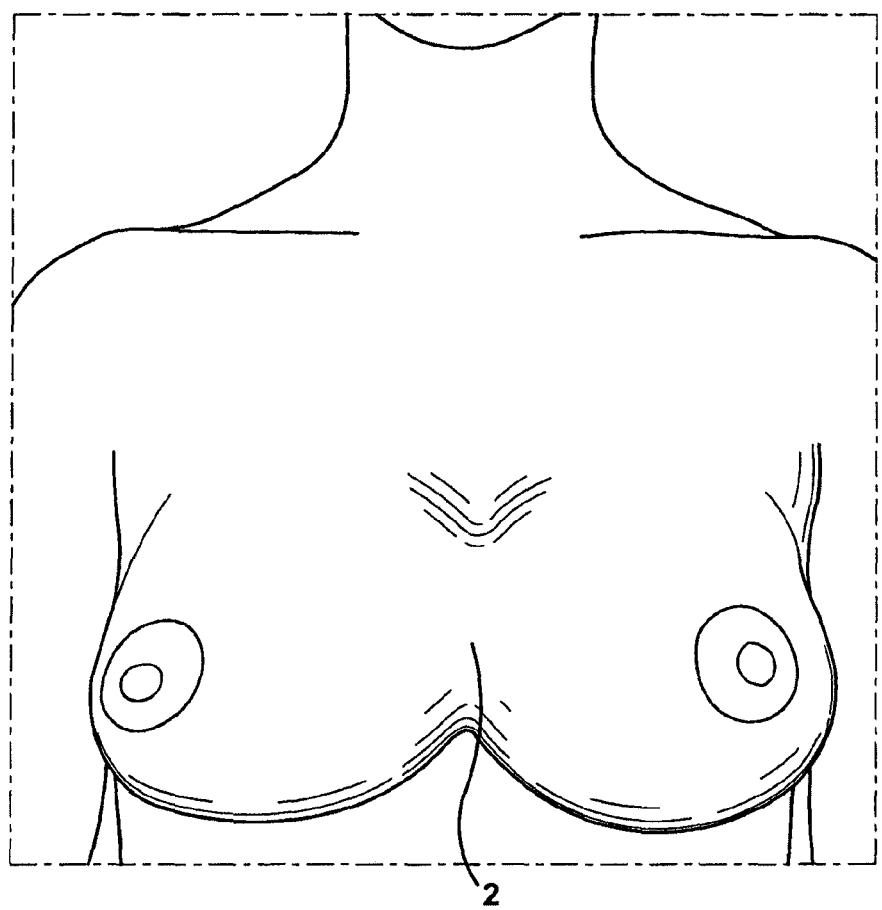
FIG. 1 shows a front elevation view of malpositioned breast implants exhibiting symmastia.
Figure 2:
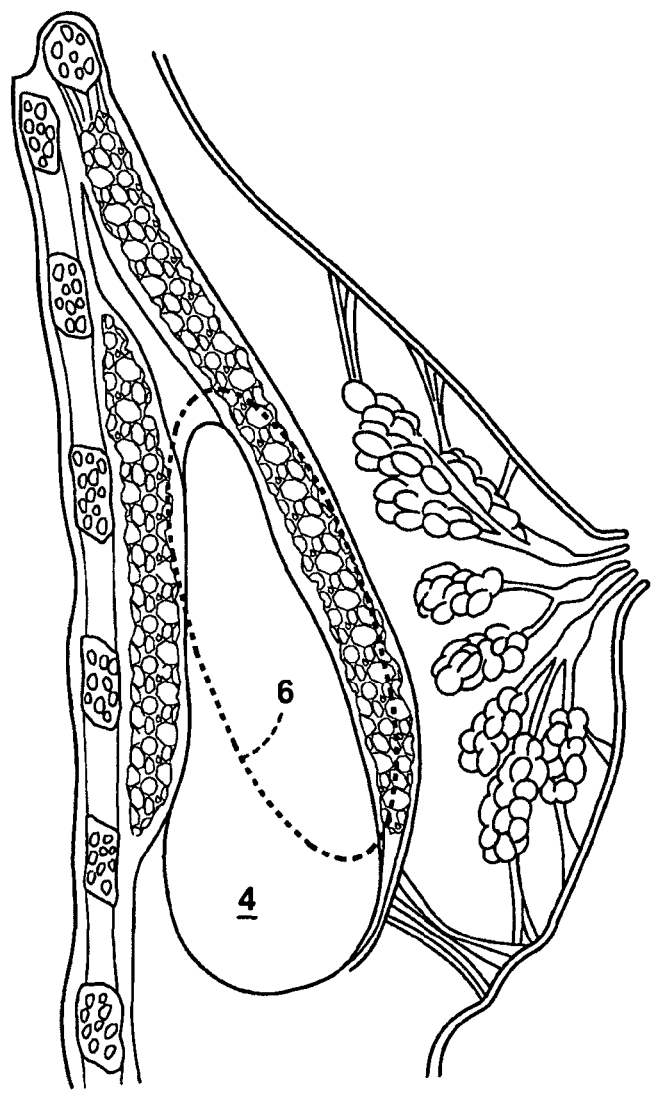
FIG. 2 shows a front elevation view of malpositioned breast implants exhibiting inferior displacement.
Figure 3:
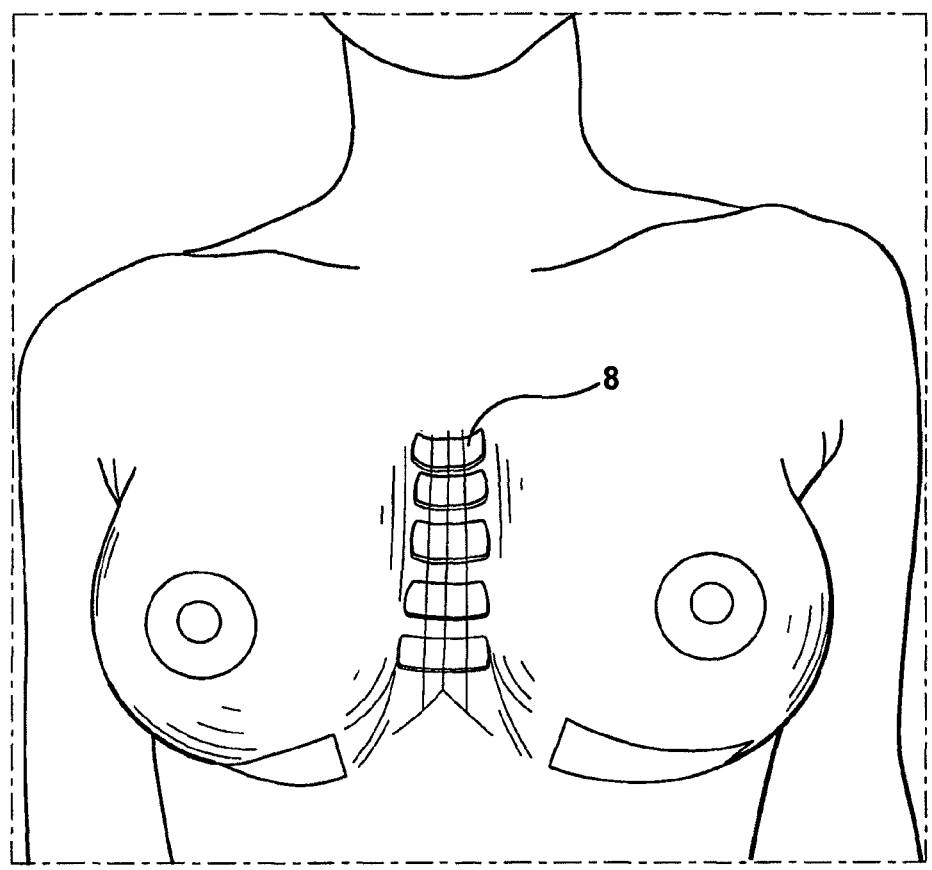
FIG. 3 shows exteriorly placed bolsters and sutures used to maintain proper implant placement after a procedure to correct symmastia.
Figure 4:
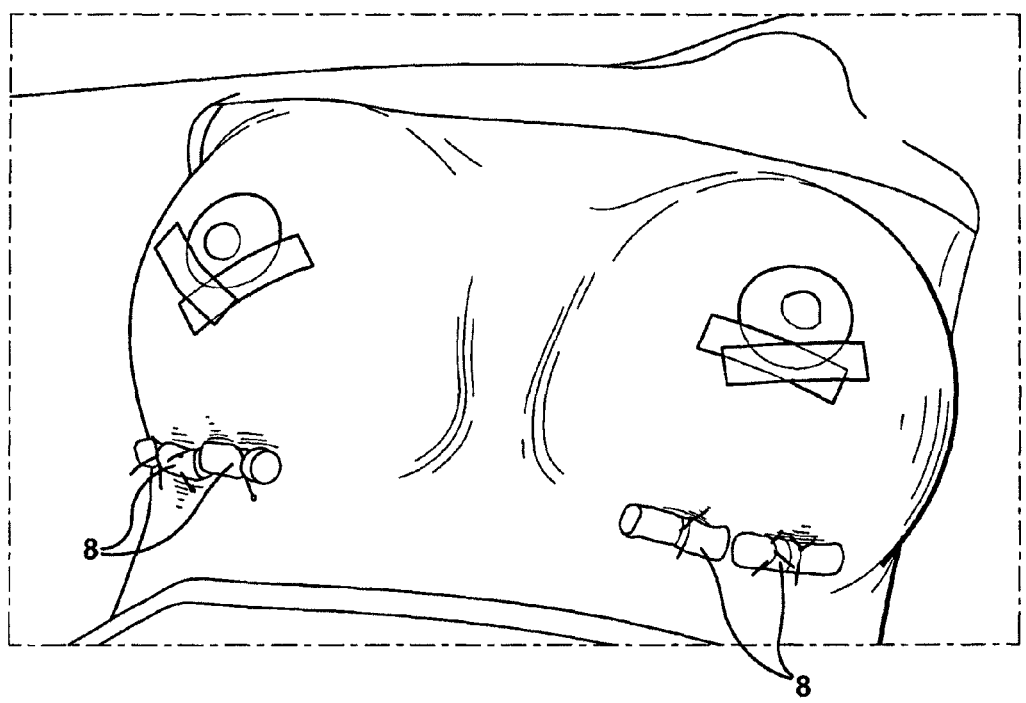
FIG. 4 shows exteriorly placed bolster and sutures used to maintain proper implant placement after a procedure to correct bottoming-out of implants.
Figure 5:
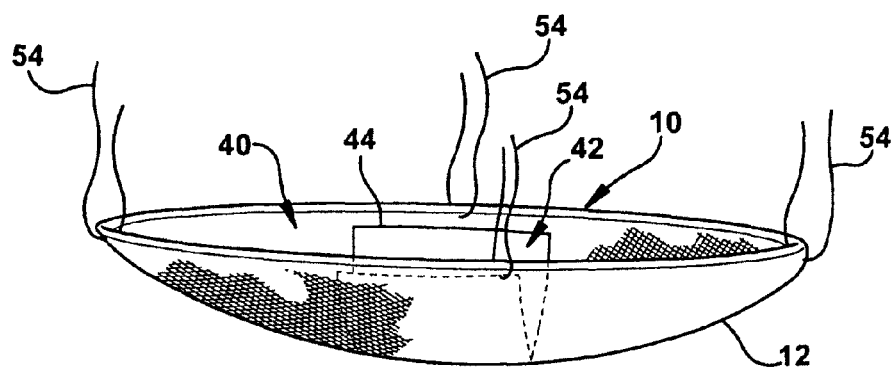
FIG. 5 shows a front elevation view of a first preferred embodiment of the implantable prosthesis of the present invention.
Figure 6:
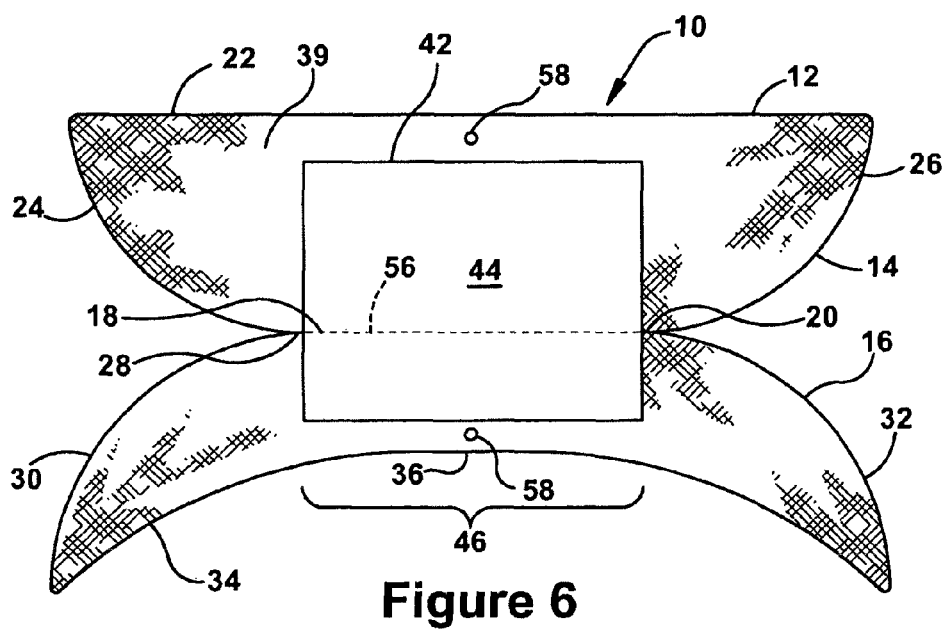
FIG. 6 shows a top plan view of a first preferred embodiment of the implantable prosthesis of the present invention.

FIGS. 5 and 6 show an exemplary embodiment of the present inventive implantable prosthesis 10. The implantable prosthesis is formed from a sheet 12 of a prosthetic material having a first and second portion 14, 16 separated by a fold line 18. The first portion 14 is substantially bowl-shaped having substantially flat, parallel bottom and top edges 20, 22, the bottom edge 20 comprises the told line 18, and curved sidewalls 24, 26 extend between the bottom and top edges 20, 22. The second portion 16 is crescent or partially C-shaped and generally mirrors the dimension and curvature of the first portion 14. The bottom edge 28 of the second portion is also at the fold line 18 and has the same dimension as and abuts the bottom edge 20 of the first portion 14. The sidewalls 30, 32 of the second portion 16 exhibit similar curvature to the corresponding sidewalls 24, 26 of the first portion 14. A concave top edge 34, having a flattened middle portion 36, interconnects the sidewalls 30, 32. The ends of the top edge 34 of the second portion 16 adjoin with the corresponding ends of the sidewalls 30, 31 to form tapered ends to the second portion 16.

The sheet of prosthetic material 12 is preferably constructed from a polypropylene mesh having pore size and density configured to promote in growth of the surrounding tissue upon placement of the implantable prosthesis within the patient. The porous nature therefore provides a tissue affixation region 38 incorporated within the prosthesis 10. The tissue affixation region 38 can also serve as the location for attachment of the implantable prosthesis to the patient through means such as tacking or suturing, described in greater detail below. In the preferred embodiment shown in FIGS. 5 and 6, the overall longitudinal length of the prosthesis is approximately 10 inches in length. The bottom edge 20, 28 of the first and second portions is approximately 4½ inches in length. The width of the first portion 14 is approximately 4½ inches and the width of the second portion 16 is at least 5½ inches. These dimensions are exemplary and enable a single-sized implantable prosthesis to be used with varying patient size and varying implant size. These dimensions also allow sufficient room for anterior and posterior incorporation while minimizing bunching or overlap of the device. It is also contemplated that use of the polypropylene mesh will enable the surgeon to cut the implantable prosthesis to size as is required depending on factors including implant volume and size, and size of the patient, without affecting the structural integrity of the device, exposing seams in the mesh ribbon, or creating rough surfaces with the potential to abrade the implant surface or irritate the surrounding tissue.

As is seen in FIG. 5, the first and second portions 14, 16 are configured to form a basket or trough-like receiving area 40 for receiving and seating the breast implant (not shown). The receiving area 42 is formed by folding the first portion 14 over the second portion 16 such that the opposing surfaces form a pocket-like structure. The sidewalls 24, 26 of the first portion 14 and the sidewalls 30, 32 of the second portion 16 are affixed together by sutures, a suitable adhesive, or tacking to maintain the shape of the implantable prosthesis. The variance between the width of the first and second portions 14, 16 determines the volume of the receiving area 40 and is dependent on the size and volume of the implant.

The implantable prosthesis 10 of the present invention also comprises a biocompatible landing 42 overlying the prosthetic material 12, where the landing 42 is adapted to communicate with and support the breast implant. Preferably the biocompatible landing 42 is composed of polytetraflouroethylene (PTFE), silicone, or any other suitable chemically inert material. In the preferred embodiment shown in FIGS. 5 and 6, the biocompatible landing 42 comprises a pad 44 overlying the receiving area 40. The pad 44 is affixed to the prosthetic material 12 by means of stitching, use of a biocompatible, inert adhesive, or any other suitable means of affixation. In this embodiment, the pad 44 is dimensioned to leave approximately ½ inch of the underlying ribbon exposed across the width of the implantable prosthesis and approximately 1 inch of the underlying mesh exposed at either end of the implantable prosthesis, so as to foster in growth of the surrounding tissue.

Figure 7:
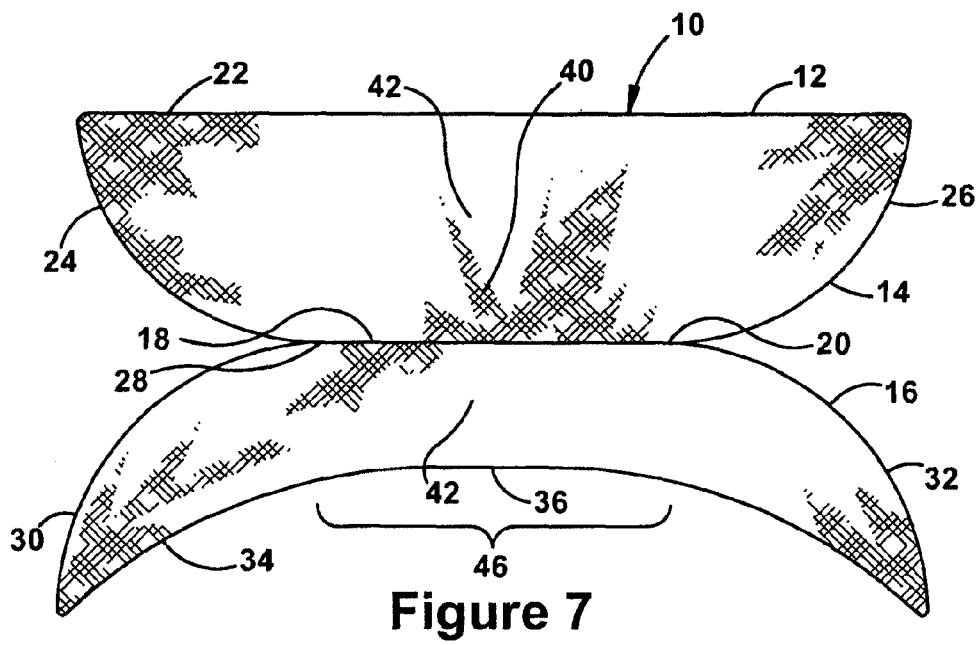
FIG. 7 shows a top plan view of a second preferred embodiment of the implantable prosthesis of the present invention.

In another preferred embodiment of the implantable prosthesis, shown in FIG. 7, the outer surface of the polypropylene mesh is coated, in at least the receiving area 40, with PTFE, silicone, or any other suitable, chemically inert material. In yet another preferred embodiment (not shown) the sheet of prosthetic material is composed entirely of a soft, biocompatible and chemically inert material with a smooth a smooth outer surface. Utilization of smooth, chemically inert materials on the outer surface of the sheet of prosthetic material will reduce the incidence of abrasion to and degradation of the shell of the breast implant as well as preventing unwanted reactions with the shell of the breast implant and surrounding tissues.

As previously mentioned, the overall dimensions of the implantable prosthesis 10 are exemplary and it is contemplated that the surgeon or medical staff preparing the prosthesis for implantation within the patient may have to modify the dimensions of the prosthesis as is needed. Referring to FIGS. 6 and 7, the substantially flat, parallel top and: bottom edges 20, 22, 28, 34 of the first and second portions 14, 16 define an adjustment area 46 where the surgeon or medical staff may remove material from the standard length prosthesis and reassemble the prosthesis without changing the overall shape of the prosthesis.

Figure 8:
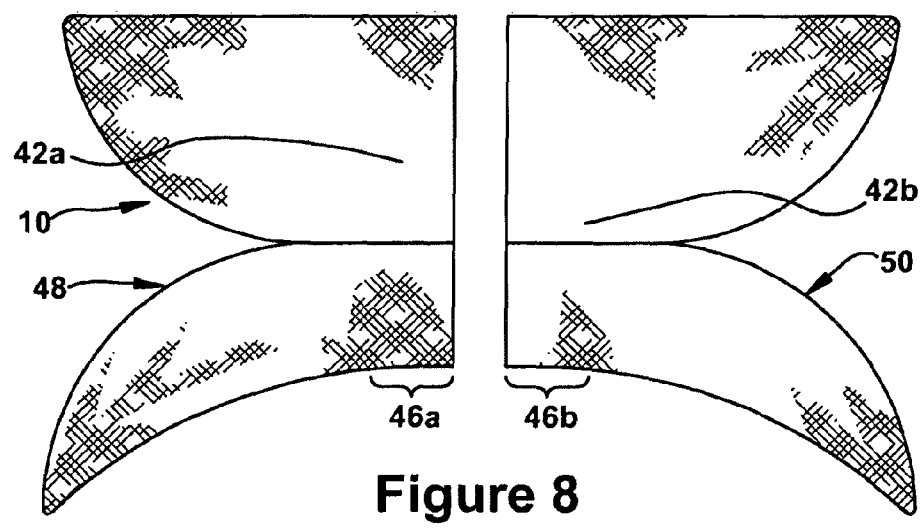
FIG. 8 shows a top plan view of a third preferred embodiment of the implantable prosthesis of the present invention.

In yet another preferred embodiment, shown in FIG. 8, the prosthesis is manufactured in substantially mirror image components 48, 50, where the components may be overlapped and assembled at the desired longitudinal length or, alternatively, material may be removed from the adjustment areas 46*a, b* of the components and the components assembled to form a prosthesis in the desired length. This flexibility results from the shape and configuration of the prosthesis. It is contemplated that in this embodiment, the landing 42*a, b* may be comprised of the pad as previously described or a coating on the fibers of the ribbon.

Yet another advantage of the present inventive implantable prosthesis over currently available corrective measures is the cost of the implantable prosthesis. It is anticipated that the mesh sheet will cost approximately a small fraction of the price of a comparably sized piece of AlloDerm® or other synthetic soft tissue replacement material.

Another aspect of the present invention is the incorporation of orientation markings on the mesh sheet and the use of different colors to identify different areas of the prosthesis. Referring to the preferred embodiment of the present invention shown in FIG. 6, the first portion 14 is generally formed in a first color and the second portion is generally formed in a second color to enable the surgeon to easily distinguish the two portions of the sheet 12. Accordingly, the colors should be easily distinguishable from each other. The sheet 12 includes a center delineation marking 56 identifying the fold line 18 and markings 58 identifying the front surface of the sheet 12.

In operation, the implantable prosthesis is cut to its desired dimensions, and then rolled into a tube or "burrito" shape to enable easy insertion into the patient through a small incision, and is tacked or sutured at both ends to hold the prosthesis in the rolled shape during surgery. During implant positioning or repositioning procedures the surgeon will likely use the initial incision made to insert the implant provided the initial incision was peri-areolar or in the inframammary fold, to access and position the implant with the implantable prosthesis. However, in certain circumstances, such as if the initial incision is in the transaxillary position, it may be necessary to create a new incision. Once the incision is made, the rolled up implantable prosthesis is inserted into the body through the incision. The suture or tack at the distal end of the implantable prosthesis is removed enabling the end to unroll, creating a fan-shaped structure.

Figure 9:
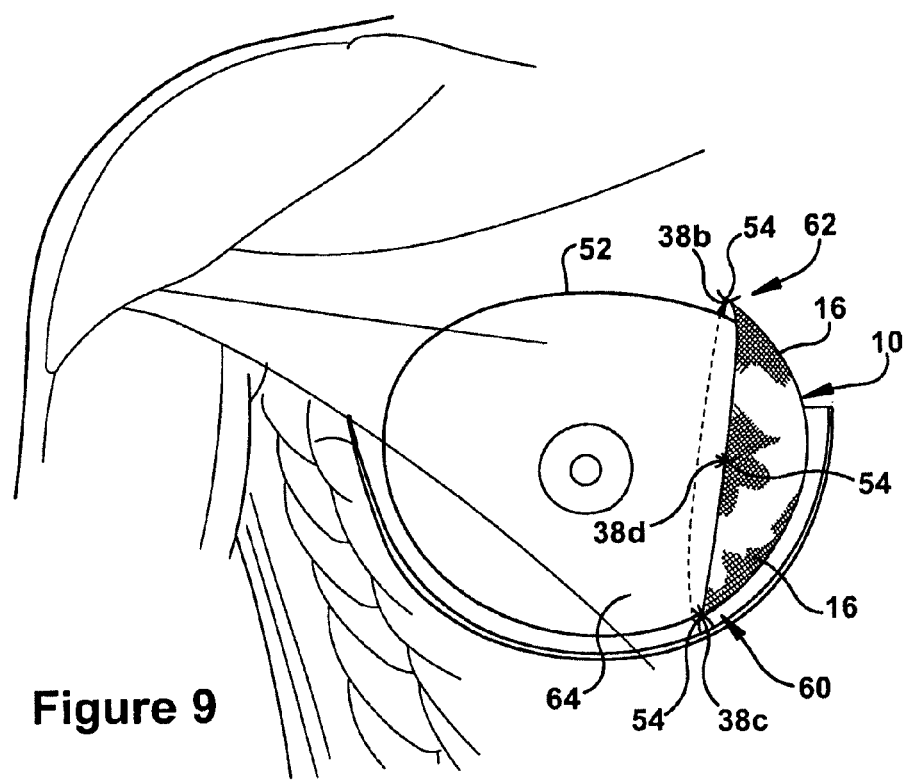
FIG. 9 shows a front elevation view of a breast implant supported by the implantable prosthesis of the present invention.
Figure 10:
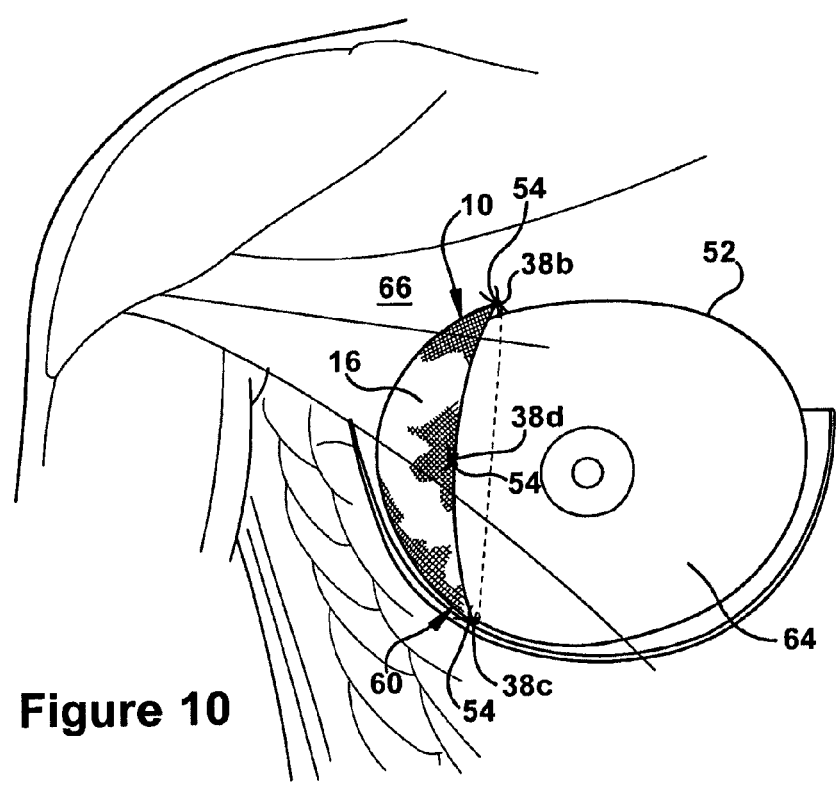
FIG. 10 shows another front elevation view of a breast implant supported by the implantable prosthesis of the present invention.
Figure 11:
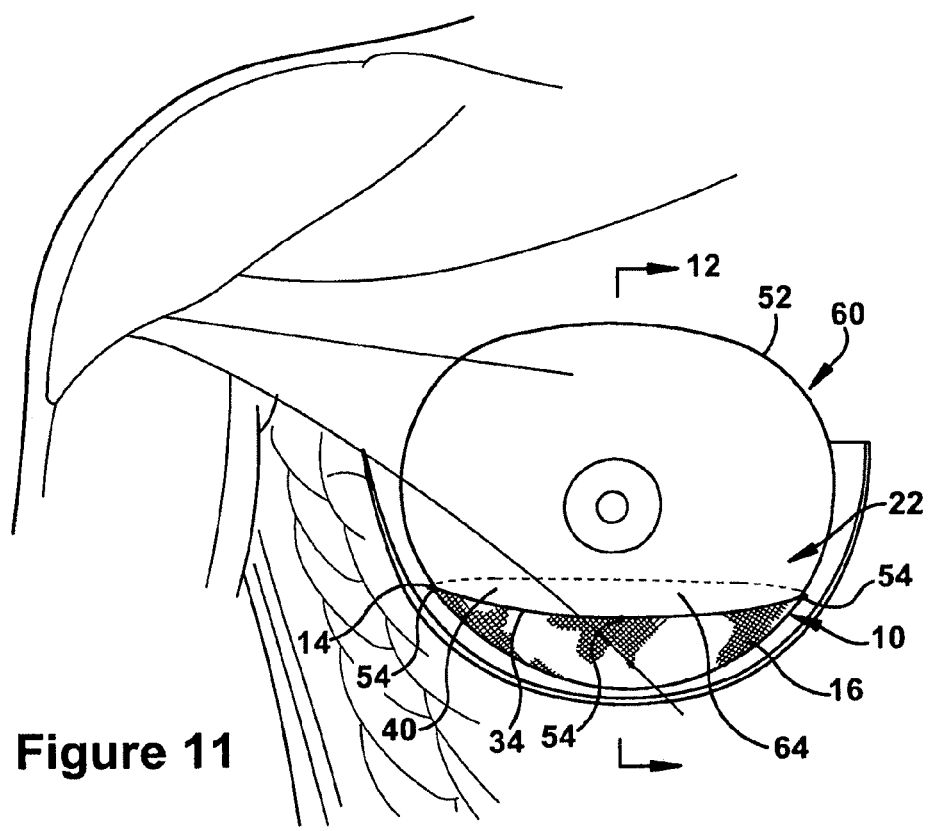
FIG. 11 shows a front elevation view of a breast implant supported by an implantable prosthesis of the present invention.
Figure 12:
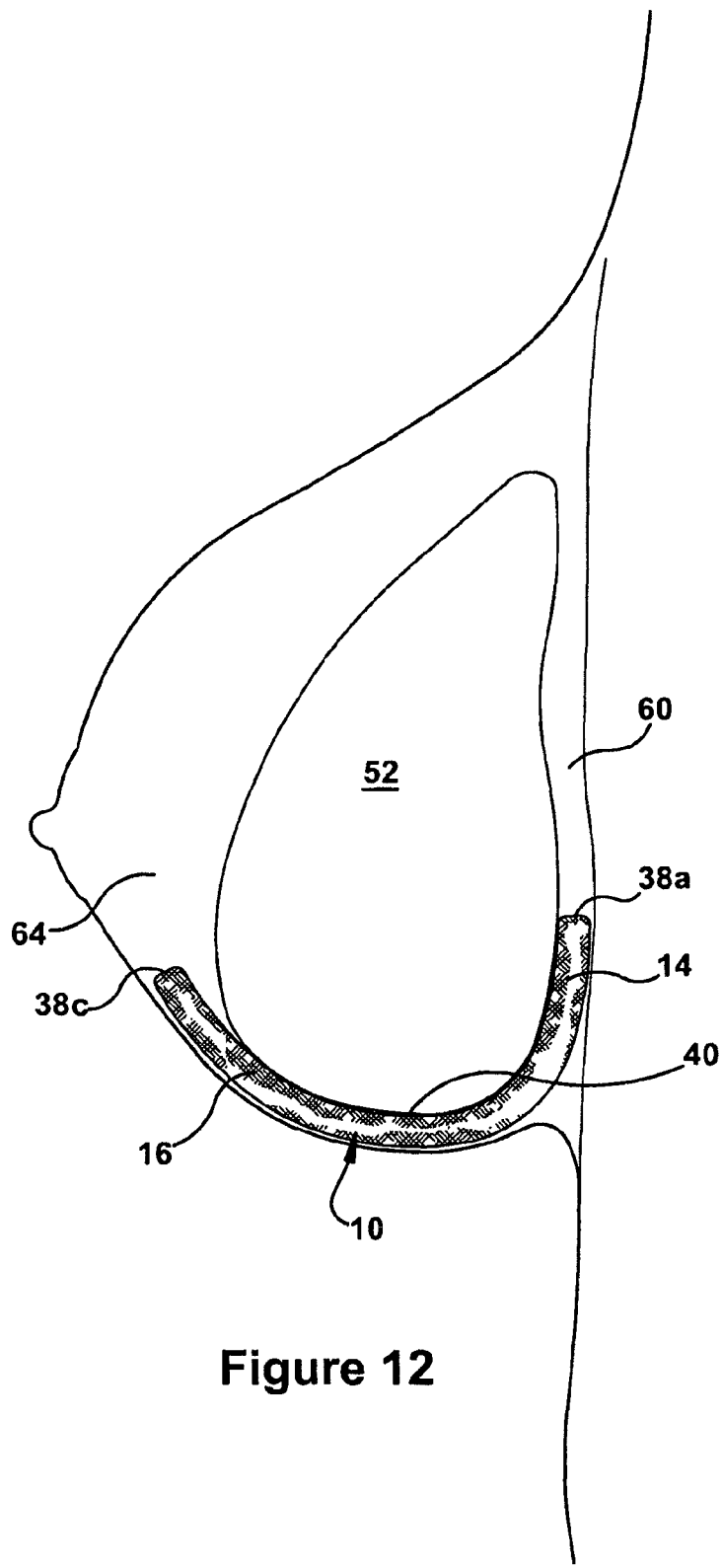
FIG. 12 is a cross-sectional view of the breast and breast implant supported by the implantable prosthesis of the present invention, the cross-section taken along line 12-12 in FIG. 11.

The implantable prosthesis of the present invention is configured to be implanted within the patient in varying orientation, depending on the specific situation to be remedied or prevented. Referring to FIGS. 9 and 10, when the implantable prosthesis 10 is used to correct medial displacement (symmastia) (FIG. 9) or lateral displacement (FIG. 10) of implant, the prosthesis is positioned in a substantially vertical position on the medial or lateral side, respectively, of the implant 52. Referring to FIGS. 11 and 12, when the implantable prosthesis 10 is used to correct inferior displacement of an implant 52 (bottoming out), the prosthesis is placed in a substantially horizontal position, supporting the implant 52 from below. Proper positioning of the implantable prosthesis during the initial implant placement procedure is dependent on the tissue structure surrounding the implant and the desired placement of the implant within the patient.

Once the implantable prosthesis is in the proper position, the second, proximal suture or tack is removed enabling the implantable prosthesis to fully unroll, exposing the receiving area. As is seen in FIG. 9-12, the back surface of the first portion 14 is positioned towards the chest cavity wall and the back surface of the second portion 16 is positioned towards the skin, with the implant 52 being received by and seated within the receiving area 40.

Fixation of the implantable prosthesis is achieved either by placement of permanent sutures 54 (FIG. 9-11) at key locations via the tissue affixation regions, or with use of a tacking device, either conventional or endoscopic, depending on the placement of the incision. An inframammary fold incision will ordinarily require suturing of the implantable prosthesis in place whereas a peri-areolar incision will enable the use of the endoscopic tacking device. FIGS. 5 and 9 show exemplary placement of sutures 54 along the top edges 22, 24 of the prosthesis. Over time, the porous nature of the ribbon will enable tissue in growth, strengthening the fixation of the implantable prosthesis by dispersing the forces exerted on the prosthesis throughout the ribbon as opposed to the suture or tacking points.

As is shown in FIG. 9, when the implantable prosthesis 10 is orientated in vertical position to fix or prevent medial displacement of the implant, the prosthesis is secured at tissue affixation regions 38*b, c, d* to the following structures and soft tissue: 1) center tissue affixation region (not shown) on the backwall to the periosteum of the chest wall 60, 2) tissue affixation region 38*b* at the upper intersection of the first and second portions to the sternal border 62 of the chest wall, 3) tissue affixation region 38*c* at the lower intersection of the first and second portions to periosteum of the chest wall 60, and 4) the center tissue affixation region 38*b* on the frontwall to the posterior aspect of the pectoralis fascia 64.

As is shown in FIG. 10, when the implantable prosthesis 10 is orientated in a substantially vertical position to fix or prevent lateral displacement of the implant 52, the prosthesis is secured at tissue affixation regions 38*b, c, d* to the following structures and soft tissue: 1) center tissue affixation region (not shown) on the backwall to the periosteum of the chest wall 60, 2) tissue affixation region 38*b* at the upper intersection of the first and second portions to the apex of the axilla 66, 3) tissue affixation region 38*c* at the lower intersection of the first and second portions to periosteum of the chest wall 60, and 4) the center tissue affixation region 38*d* on the frontwall to the posterior aspect of the pectoralis fascia 64.

As shown in FIGS. 11-12, when the implantable prosthesis 10 is orientated in a substantially horizontal position to fix or prevent interior displacement of the implant 52, the prosthesis is secured at tissue affixation regions 38*a, b, c, d* to the following structures and soft tissue: 1) center tissue affixation region 38*a* on the backwall to the periosteum of the chest wall 60, 2) tissue affixation region 38*b* at lateral intersection of the first and second portions to the periosteum of the chest wall 60, 3) tissue affixation region 38*c* at the medial intersection of the first and second portions to the periosteum of the chest wall 60, and 4) the center tissue affixation region 38*d* on the frontwall to the posterior aspect of the pectoralis fascia 64.

Figure 13:
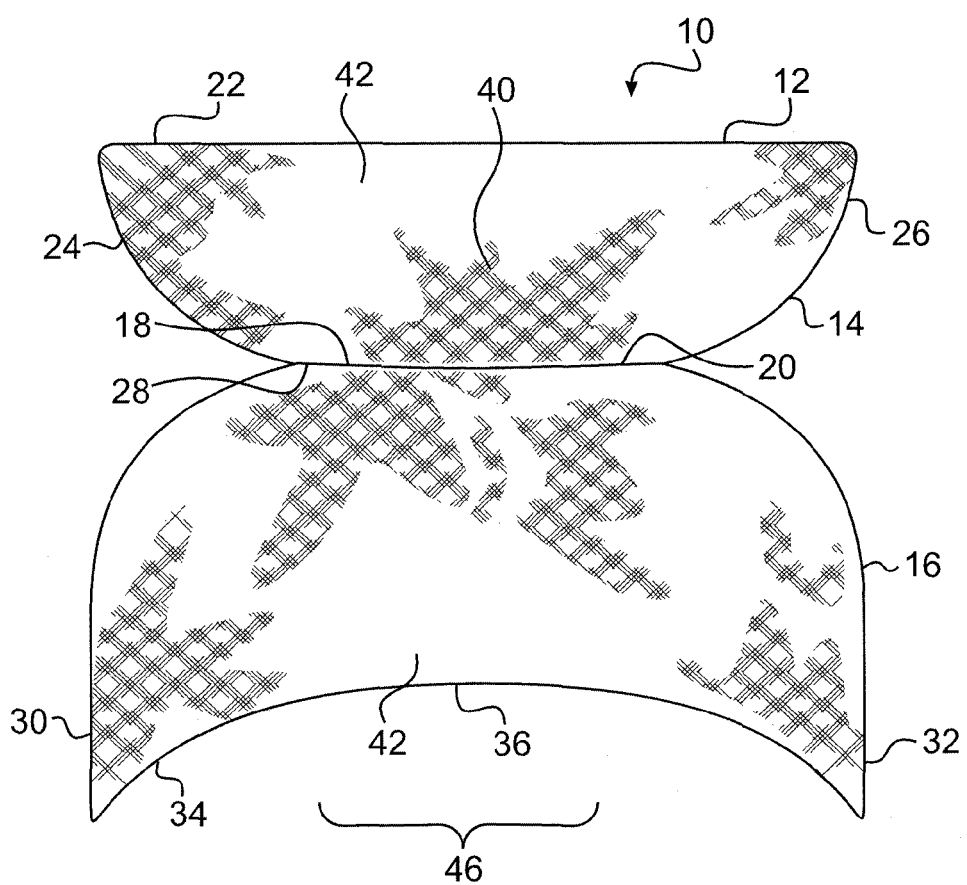
FIG. 13 shows a top plan view of a fourth preferred embodiment of the implantable prosthesis of the present invention.
Figure 14:
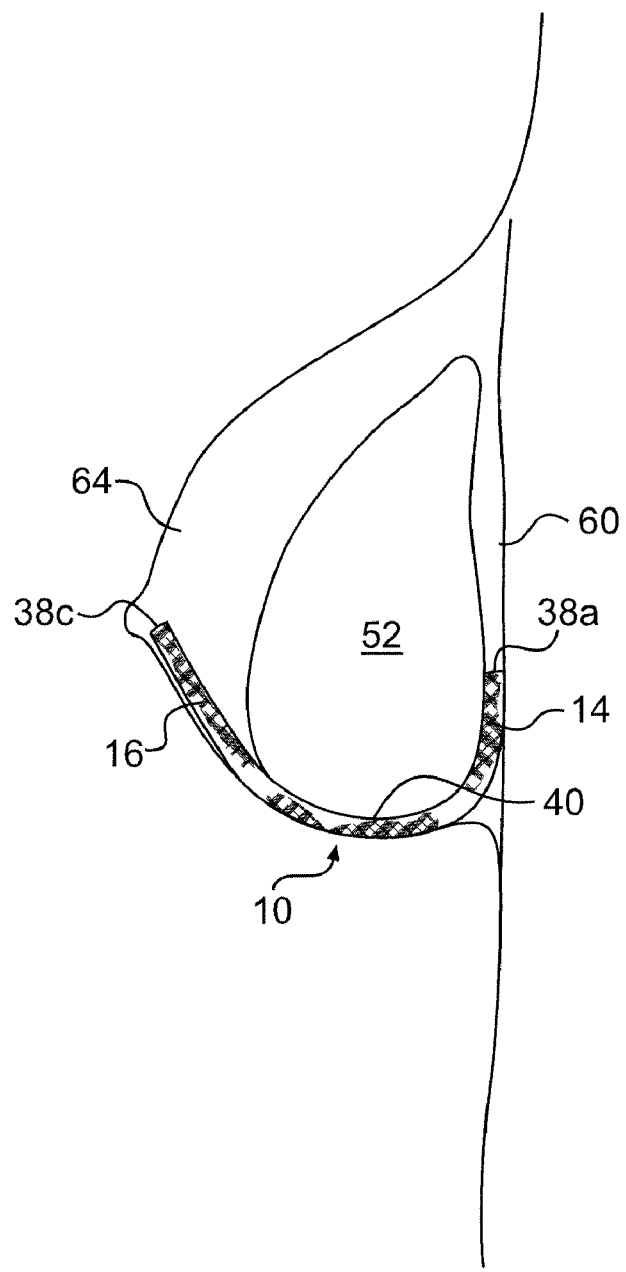
FIG. 14 is a cross-sectional view of the breast and breast implant supported by the implantable prosthesis of the fourth preferred embodiment of the present invention.

Another embodiment of the preferred invention is shown in FIGS. 13 and 14. In this embodiment, and in contrast to the previously discussed embodiments, the sidewalls of the first and second portions are not substantially the same height, relative to the fold line 18 and bottom edge 28. Instead, the width of second portion 16 is increased, preferably one or more inches, relative to the embodiment of FIG. 7, for example. As a result, and as shown in FIG. 14, placement of the prosthesis inferior to and supporting, implant 52, results in an anterior wall of the prosthesis being higher in elevation that the posterior wall of the prosthesis. This embodiment of the present invention is particularly well suited for use in breast reconstruction postmastectomy. In addition to supporting the implant, the enlarged anterior wall 16 also assists in defining the shape and contour of the reconstructed breast.

The embodiment of the present invention having a larger anterior wall portion 16 has so far been illustrated as being constructed of polypropylene mesh or other porous material, with an outer surface coated, at least in the receiving area 40, with PTFE, silicone, or other chemically inert material. However, embodiments of the present invention having a larger anterior wall portion may also be constructed polypropylene mesh or other porous material, with a biocompatible landing area of PTFE, silicone or other chemically inert material, as illustrated, for example in FIG. 6. Moreover, in addition to the unitary construction of FIG. 13, the embodiments of the present invention having a larger anterior wall portion, may alternatively be constructed of substantially mirror image components as depicted, for example, in FIG. 8.

Moreover, in additional preferred embodiments of the present invention, a biologic mesh may be substituted for some, or all, of the polypropylene mesh previously discussed. The biologic mesh typically comprises an acellular dermal matrix, comprising skin from which the epidermis, as well as antigens which may lead to tissue rejection, have been removed. The acellular matrix may be of porcine origin, or may be derived from human donor tissue, such as the ALLO-DERM acellular dermal matrix sold by LifeCell Corporation. Alternatively, a portion, or all, of the surface of a mesh of polypropylene or other suitable porous material may be covered with a biologic mesh or dermal matrix material. In this manner, the polypropylene mesh will serve to add additional framework and support for the biologic mesh material.

The implantable prosthesis described herein is applicable across a wide range of procedures involving breast implants, both in connection with implant repositioning procedures, in a prophylactic nature at the time of initial implant placement to prevent displacement, in subsequent corrective procedures in the future, as well as, for certain embodiments of the present invention, breast reconstruction postmastectomy. Prophylactic use will be particularly applicable in bariatric patients who have lost significant amounts of weight. These patients will typically exhibit very poor soft tissue support and significant loss of breast volume. These factors, combined with bariatric patients being accustomed to a larger breast size, tend to result in a larger implant that cannot be properly supported by existing tissue structures. Application of the implantable prosthesis of the present invention during, the initial breast augmentation procedure will greatly reduce, if not eliminate post-operative implant displacement and the need for post-operative corrective procedures.

It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A prosthesis implantable with a patient comprising:
    a sheet of prosthetic material configured to form a concavity having an interior surface and an exterior surface;
    a breast implant positioned within said interior surface of said concavity such that a portion of said prosthetic material is positioned between a portion of said breast implant and a chest cavity;
    wherein said interior surface supports said breast implant such that a portion of said breast implant partially projects from said concavity.

2. The prosthesis of claim 1 further comprising:
    a tissue affixation region along said exterior surface, said tissue affixation region adapted to be affixed to said patient.

3. The prosthesis of claim 2, wherein a portion of said tissue affixation region is adapted to be affixed to said patient on opposing sides of said breast implant.

4. The prosthesis of claim 2, wherein said tissue affixation region is adapted to attach said prosthesis to soft tissue surrounding the breast implant or a boney structure or a chest wall in said patient with a suture.

5. The prosthesis of claim 2, wherein said tissue affixation region is adapted to attach said prosthesis to soft tissue surrounding the breast implant or a boney structure or a chest wall in said patient by tacking.

6. The prosthesis of claim 4, wherein said suture is attached through capsular tissue.

7. The prosthesis of claim 1 further comprising a biocompatible landing overlying at least a portion of said prosthesis, said landing capable of receiving and supporting said breast implant.

8. The prosthesis of claim 7, wherein said landing is composed of a material selected from the group consisting of polytetrafluoroethylene and silicone.

9. The prosthesis of claim 1, wherein said exterior surface comprises a biocompatible material.

10. The prosthesis of claim 1, wherein said interior surface comprises a biocompatible material.

11. The prosthesis of claim 1, wherein said prosthesis is configured to position said breast implant in completely sub-muscular, partial sub-muscular, or sub-glandular placement within said patient.

12. The prosthesis of claim 1, wherein said concavity is positioned to hold said breast implant in its desired location.

13. The prosthesis of claim 1, wherein said concavity is configured to enclose a portion of said breast implant.

\* \* \* \* \*